United States Patent [19]

Haffer et al.

[11] Patent Number: 4,826,852
[45] Date of Patent: May 2, 1989

[54] NOVEL ERGOLINYL COMPOUNDS NITROGEN-SUBSTITUTED IN THE 8-POSITION, USEFUL FOR TREATING DOPAMINE DEFICIENCY

[75] Inventors: Gregor Haffer; Gerhard Sauer; Helmut Wachtel; Herbert Schneider; Ulrich Eder, all of Berlin, Fed. Rep. of Germany

[73] Assignee: Schering Aktiengesellschaft, Berlin and Bergkamen, Fed. Rep. of Germany

[21] Appl. No.: 878,762

[22] Filed: Jun. 26, 1986

Related U.S. Application Data

[63] Continuation of Ser. No. 452,521, Dec. 23, 1982, abandoned.

[30] Foreign Application Priority Data

Dec. 23, 1981 [DE] Fed. Rep. of Germany ....... 3151912

[51] Int. Cl.[4] ..................... A61K 31/44; A61K 31/54; C07D 457/12; C07D 417/14
[52] U.S. Cl. ...................................... 514/288; 546/68; 514/253; 514/228.2; 514/232.8; 544/58.4; 544/61; 544/125; 544/361
[58] Field of Search ................... 546/67; 514/285, 222, 514/228, 253; 544/58.4, 125, 361

[56] References Cited

U.S. PATENT DOCUMENTS

| | | | |
|---|---|---|---|
| 2,533,698 | 12/1950 | Stoll | 546/68 |
| 2,864,822 | 12/1958 | Fornefeld et al. | 546/67 |
| 3,717,640 | 2/1973 | Acari | 546/68 |
| 4,348,391 | 9/1982 | Fehr | 546/68 |
| 4,348,392 | 9/1982 | Fehr | 546/68 |
| 4,500,712 | 2/1985 | Bernardi et al. | 546/67 |
| 4,740,509 | 4/1988 | Sauer et al. | 514/288 |

FOREIGN PATENT DOCUMENTS

| | | |
|---|---|---|
| 0021206 | 1/1981 | European Pat. Off. |
| 1567484 | 5/1980 | United Kingdom |
| 2081262 | 2/1982 | United Kingdom |

OTHER PUBLICATIONS

Wachtel et al., Life Science, vol. 32, pp. 421–432 (1983).
Chemical Abstracts, Vol. 104, 1986, Page 499, Abstract No. 19724b.

Primary Examiner—Robert Gerstl
Assistant Examiner—Cecilia A. Shen
Attorney, Agent, or Firm—Millen & White

[57] ABSTRACT

Ergolinyl compounds which are nitrogen-substituted in the 8-position and have Formula (I)

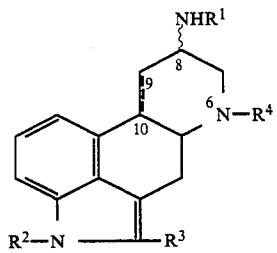

and physiologically compatible salts thereof, wherein
(a) $R^1$ is hydrogen, the 8-substituent can be in the α- or β-position and

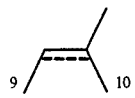

represents a single or a double bond,
$R^2$ is hydrogen, $C_{1-4}$-alkyl or $C_{1-7}$-acyl,
$R^3$ is hydrogen, chlorine or bromine, and
$R^4$ is $C_{1-6}$-alkyl, $C_{3-6}$-cycloalkyl-$C_{1-3}$-alkyl, $C_{3-6}$-alkenyl, or $C_{3-6}$-alkynyl; or
(b) $R^1$ is

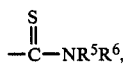

and the 8-substituent can be in the α- or β-position,

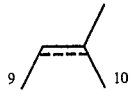

represents a single or double bond,
$R^2$, $R^3$ are as defined above,
$R^4$, is $C_{1-6}$-alkyl, $C_{3-6}$-cycloalkyl-$C_{1-3}$-alkyl, $C_{3-6}$-alkenyl, or $C_{3-6}$-alkynyl; and
$R^5$ is hydrogen, $C_{-10}$-alkyl, $C_{3-10}$-alkenyl, or $C_{3-10}$-alkynyl, and
$R^6$ is $C_{1-10}$-alkyl, $C_{3-10}$-alkenyl, $C_{3-10}$-alkynyl, or aryl, or
$R^5$ and $R^6$ together with the connecting N-atom form a 5- to 10-membered heterocyclic ring, preferably 5- or 6-membered, which optionally can contain further heteroatoms.

31 Claims, No Drawings

NOVEL ERGOLINYL COMPOUNDS NITROGEN-SUBSTITUTED IN THE 8-POSITION, USEFUL FOR TREATING DOPAMINE DEFICIENCY

This is a continuation of application Ser. No. 452,521 filed Dec. 23, 1982 now abandoned.

The present invention relates to novel ergolinyl compounds nitrogen-substituted in the 8-position, as well as to their preparation according to conventional methods and to medicinal agents based on these compounds.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been attained by providing ergolinyl compounds which are nitrogen-substituted in the 8-position and have Formula (I)

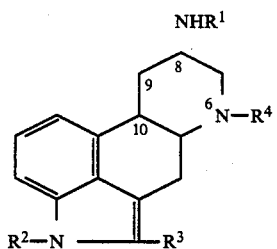

and physiologically compatible salts thereof, wherein
(a)
$R^1$ is hydrogen and the 8-substituent can be in the α- or β-position;

represents a single or a double bond,
$R^2$ is hydrogen, $C_{1-4}$-alkyl or $C_{1-7}$-acyl,
$R^3$ is hydrogen, chlorine or bromine, and
$R^4$ is $C_{1-6}$-alkyl, $C_{3-6}$-cycloalkyl-$C_{1-3}$-alkyl, $C_{3-6}$-alkenyl, or $C_{3-6}$-alkynyl or
(b)
$R^1$ is

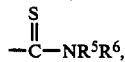

and the 8- substituent can be in the α- or β-position,

represents a single or double bond,
$R^2$, $R^3$ are as defined above,
$R^4$ is $C_{1-6}$-alkyl, $C_{3-6}$-cycloalkyl-$C_{1-3}$-alkyl, $C_{3-6}$-alkenyl, or $C_{3-6}$-alkynyl, and $R^5$ is hydrogen, $C_{1-10}$-alkyl, $C_{3-10}$-alkenyl, or $C_{3-10}$-alkynyl, and
$R^6$ is $C_{1-10}$-alkyl, $C_{3-10}$-alkenyl, $C_{3-10}$-alkynyl, or aryl, or
$R^5$ and $R^6$ together with the connecting N-atom form a 5- to 10-membered heterocyclic ring, preferably 5- or 6-membered, which optionally can contain further heteroatoms.

DETAILED DISCUSSION

All alkyl residues, according to the mentioned number of C-atoms in each case, are those derived from the corresponding aliphatic hydrocarbons, such as, for example, of up to 5 C-atoms, e.g., methyl, ethyl, n-propyl, isopropyl, n-butyl, isobutyl, tert-butyl, n-pentyl, cyclopentyl, or also of up to 10 C-atoms, e.g., hexyl, heptyl, octyl, nonyl, 1,2-dimethylheptyl, decyl, cyclohexyl, etc.

Examples of suitable aklenyl or alkynyl groups of 3–6 and up to 10 carbon atoms, respectively, include 2-propenyl, 3-methyl-2-propenyl, 2-propynyl and the like. Usually, 3–4 C-atoms are included.

The expression $C_{3-6}$-cycloalkyl-$C_{1-3}$-alkyl is understood to mean cycloalkyl-substituted alkyl groups, such as, for example, cyclopropylmethyl, cyclopentylmethyl, and cyclohexylethyl, with the point of attachment to the ring N-atom being via the acyclic alkyl portion.

Suitable acyl groups of up to 7 carbon atoms are derived from physiologically compatible acids, such as $C_{1-7}$ hydrocarbon carboxylic or sulfonic acids and many well known equivalents such as, for example, $C_{1-7}$-alkanoyl groups derived from acetic acid, propionic acid, butyric acid, valeric acid and the like, or $C_{1-7}$-aromatic acyl groups derived from benzoic acid, p-toluenesulfonic acid, etc.

Suitable aryl groups are of 6–10 C-atoms, such as optionally substituted phenyl groups wherein suitable substituents include lower alkyl or lower alkoxy groups (lower=1–4 C-atoms), or halogen, such as F, Cl, or Br.

For $R^5$ and $R^6$, the alkyl groups preferably contain 1–2 C-atoms; and the alkenyl and alkynyl groups preferably contain 3–4 C-atoms.

When the substituents $R^5$ and $R^6$ together form a preferably aliphatic saturated heterocyclic ring with the connecting N-atom, suitable groups include pyrrolidinyl and piperidyl. Replacement of a $CH_2$-group in these rings is also possible, e.g., by an O, S, or N atom, thereby including rings such as, for example, imidazolidinyl, imidazolinyl, pyrazolidinyl, pyrazolinyl, piperazinyl, morpholinyl, thiomorpholinyl, isothiazolidinyl, etc.

Suitable physiologically compatible salts of the compounds of Formula I (and also of II) of this invention include acid addition salts and are derived from physiologically acceptable acids which form physiologically acceptable salts of the compounds. Such physiologically acceptable acids include inorganic acids, such as, for example, hydrochloric acid, nitric acid, phosphoric acid, sulfuric acid, hydrobromic acid, hydriodic acid, nitrous acid, or phosphorous acid, or organic acids, such as, for example, aliphatic mono- or dicarboxylic acids, phenyl-substituted alkanecarboxylic acids, hydroxyalkanecarboxylic acids, or alkanedicarboxylic acids, aromatic acids, or aliphatic or aromatic sulfonic acids. Physiologically acceptable salts of these acids are, therefore, e.g., the sulfate, pyrosulfate, bisulfate, sulfite, bisulfite, nitrate, phosphate, monohydrogen phosphate, dihydrogen phosphate, metaphosphate, pyrophosphate, chloride, bromide, iodide, fluoride, acetate, propionate, decanoate, caprylate, acrylate, formate, isobutyrate, caproate, heptanoate, propiolate, malonate, succinate, suberate, sebacate, fumarate, maleate, mandelate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β-hydroxybutyrate, glycollate, malate, tartrate, methanesulfonate, propanesulfonate, naphthalene-1-sulfonate, or naphthalene-2-sulfonate.

As compared with known ergolines, such as, for example, lisuride hydrogen maleate, the compounds of this invention are distinguished, e.g., as shown in animal experiments, by higher efficacy, longer duration of activity, and lower acute toxicity. The compounds predominantly affect central dopamine receptors, on which they can act in an agonistic and/or antagonistic fashion. The direct dopaminergic effectiveness of the compounds shows them to be valuable compounds for the treatment of dopamine deficiency conditions of the central nervous system, for example, for treatment of parkinsonism, certain forms of dementia, and in hyperprolactinemia. Because of the preferential stimulation of certain dopamine receptor subpopulations, dopaminergic routes of the central nervous system can be influenced selectively, thus lessening the risk of undesirable side effects.

Their antidopaminergic activity shows the compounds to be valuable neuroleptics for the treatment of psychoses of the schizophrenic array of disorders, see, e.g., Schizophrenia, Biological and psychological Perspectives (Ed. G. Uschin), Brunner/Mazel, N.Y. 1975 whose disclosure is incorporated by reference herein. The partial dopaminergic effect inherent in the compounds causes the undesirable side effects of classical, dopamine-receptor-blocking neuroleptics (e.g., butyrophenones, phenothiazines), such as, for example, extra-pyrimidal-motoric movement anomalies or hyperprolactinemia, to be diminished or avoided.

As described in the followinbg references, observation of both agnostic and antagonistic effects at the same time for a given class of drugs is not unusual in this area of activity. See for reference, A. Enz, Life Sci., 29, 2227–2234 (1981) Biphasic Influence of a 8α-Amino Ergoline, CU 32-085, on Striatal Dopamine Synthesis and Turnover in vivo in the Rat; H. Wachtel, Central Dopaminergic and Antidopaminergic Effects of Ergot Derivatives Structurally Related to Lisuride in "Lisuride and other Dopamine Agonists", eds. Calne, D. B., Horowski, R., McDonald, R. J. Wuttke, W.; Raven Press N.Y. pp. 109–125 (1983); H. Wachtel and R. Dorow, Dual Action on Central Dopamine Function of Transdihydrolisuride, a 9,10-Dihydrogenerated Analogue of the Ergot Dopamine Agonist Lisuride, Life Sci., Vol. 32, pp. 421–432.

In addition, the compounds of this invention act on central noradrenaline and serotonin receptors. This activity, in addition to the dopaminergic activity, shows the compounds to be valuable agents for the treatment of emotional and psychomotoric conditions of insufficiency due to aging, e.g., attendant to benign senile dementia.

The compounds of this invention wherein $R^1=H$ (ergolinyl-8-amines) have, for example, central and/or peripheral dopaminergic effects and thus are suitable for treatment of dopamine deficiency conditions of the CNS system and/or for lowering blood pressure.

The indications for which the compounds are useful such as those mentioned above will be conventionally apparent to skilled workers.

The effectiveness of the compounds of this invention was determined by radioimmunoassay through detection of the prolactin concentration in the serum of small rodents upon intraperitoneal administration, and by analysis of test animal behavior. According to studies by Anden et al, the occurrence of stereotypic motor activity in mice and rats, e.g., chewing, gnawing, and licking, even after depletion of the monoamine stores with reserpine (5 mg/kg i.p. 24 hours before testing), together with elimination of immobility caused by reserpine, can be directly considered as an indication of dopamine-receptor-stimulating activity (Anden, N.-E., Stroembom, U., and Svensson, T. H.: Dopamine and Noradrenaline Receptor Stimulation: Reversal of Reserpine-Induced Suppression of Motor Activity, Psychopharmacologia 29: 289, 1973, whose disclosure is incorporated by reference herein).

For utilization, e.g., for administration as medicinal agents to mammals including humans, the compounds of this invention are converted into the form of a pharmaceutical preparation containing, in addition to the active ingredient, pharmaceutical, organic or inorganic inert excipients suitable for enteral or parenteral administration, such as, for example, water gelatin, gum arabic, lactose, amylose, magnesium stearate, talc, vegetable oils, polyalkylene glycols, etc. The pharmaceutical preparations can be present in solid form, e.g., as tablets, dragees, suppositories, capsules, or in liquid form, e.g., as solutions, suspensions, or emulsions. They optionally contain, in addition, auxiliary agents, such as preservatives, stabilizers, wetting agents, or emulsifiers, salts for changing the osmotic pressure, or buffers.

Usually, for the uses described above, the daily dosage of the compounds of this invention is 0.1–10 mg. Suitable unit dosages are 0.05–2 mg. Generally, the administration of the compounds of this invention is analogous to that of the known agents.

3-(D-9,10-didehydro-6-methyl-8α-ergolinyl)-1,1-diethylurea hydrogen maleate (=lisuride hydrogen maleate) and 8β-methylthiomethyl-6-propylergoline monomethanesulfonate (=pergolide mesylate).

The present invention furthermore concerns a process for preparing the compounds of this invention comprising:

for the compounds of Formula (I), wherein $R^1$ is hydrogen, in a manner known per se, (a) reacting a compound of Formula (II)

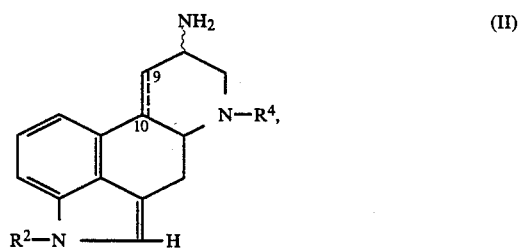

wherein the 8-amino group can be in the α- or β-position and the bond

and $R^2$ and $R^4$ are as defined above with a halogenating agent which releases chlorine or bromine; or (b) first reacting a compound of Formula (III)

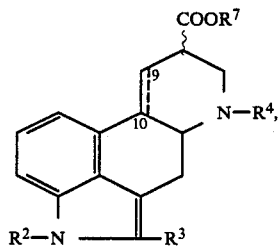

wherein the 8-positioned substituent can be in the α- or β-position, the bond

$R^2$, $R^3$, and $R^4$ are as defined above, and $R^7$ is $C_{1-16}$-alkyl, with hydrazine to form the acid hydrazide; subsequently reacting the latter with nitrous acid to form the acid azide; converting the latter by heating into the isocyanate; and heating the latter with an aqueous acid in a "Curtius decomposition"; or (c) reacting a compound of Formula (IV)

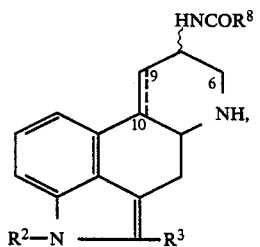

wherein the 8-positioned substituent is in the α- or β-position, the bond

$R^2$, and $R^3$ are as defined above, and $R^8$ is a $C_{1-6}$-alkyl residue, in a polar solvent with an alkylating reagent $R^4$—X wherein X is halogen, —$OSO_3C_{1-2}$-alkyl, or —O—$SO_2$—$C_6H_4$—$R^9$ (wherein $R^9$ is hydrogen or methyl) and $R^4$ is as defined above; and subjecting the resultant 6-alkyl compound to amide cleavage; and optionally, to produce compounds of Formula (I) wherein $R^1$ is

reacting the thus obtained compounds of Formula (I) wherein $R^1$ is hydrogen (d) in succession with 1,1'-thiocarbonyldiimidazole and then with an amine of the formula $HNR^5R^6$, wherein $R^5$ and $R^6$ are as defined above; or (e) with an isothiocyanate of Formula (V)

$$R^6—N=C=S \qquad (V)$$

wherein $R^6$ is $C_{1-10}$-alkyl, $C_{3-10}$-alkenyl, $C_{3-10}$-alkynyl, or aryl, and optionally, acylating the thus-produced compounds of Formula (I) wherein $R^1$ is H or —CS—$NR^5R^6$, and/or converting them into their salts.

To produce the compounds of Formula (I) of this invention wherein $R^1$ is hydrogen according to process version (a), the starting compound of Formula (II) is reacted according to methods known to those skilled in the art with 1-3 equivalents of a suitable bromine- or chlorine-releasing halogenating agent, such as, for example, bromine, pyrrolidone hydroperbromide, pyridinium hydroperbromide, or N-bromosuccinimide or N-chlorosuccinimide, N-chlorosaccharin, N-2,6-trichloro-4-nitroacetanilide, or sulfuryl chloride, in a solvent suitable for halogenations, such as dioxane, diethyl ether, tetrahydrofuran, methylene chloride, or acetonitrile, optionally in the presence of a Lewis acid, such as boron trifluoride etherate. The product is then worked up and purified by chromatography if necessary.

If process version (b) is used for preparing the compounds of Formula (I) wherein $R^1$ is hydrogen, the carboxylic acid ester in the 8-position is converted into the amine, which can be done by Curtius decomposition known to those skilled in the art. In this process, the ester is converted into the corresponding carboxylic acid hydrazide by reaction with hydrazine in a suitable solvent, such as methylene chloride or chloroform at a temperature of 0° C. to 30° C.; this hydrazide yields the carboxylic acid azide by reaction with diazotizing reagents, such as, for example, nitrous acid in an aqueous medium, or nitrosyl sulfate, nitrosyl chloride, or isoamyl nitrite with exclusion of water; in this step, benzene or tetrahydrofuran can be added to facilitate dissolution.

Rearrangement of the azide into the amine takes place with nitrogen being split off, passing through the stages of the isocyanate and carbamic acid derivatives. This last reaction step is conducted heating the solution to 50°-80° C.; termination of the reaction is controlled with the aid of thin-layer chromatography.

In order to introduce the 6-alkyl residue $R^4$ according to process version (c), blocking of the 8-amino group is required; this takes place preferably by conventional amide formation. The 8-amides of Formula (IV) are reacted in a polar solvent, such as nitromethane, methylene chloride, tetrahydrofuran, acetonitrile, or dimethylformamide with the addition of anhydrous alkaline compounds, e.g., such as sodium carbonate or potassium carbonate or sodium hydroxide with the alkylating reagent $R^4$—X, such as, for example, an alkyl halide or dialkyl sulfate, at a temperature of 10°-30° C.; the course of the reaction is controlled by thin-layer chromatography. After completion of the reaction, the mixture is evaporated to dryness and the residue is purified.

When it is desired to produce the compounds of Formula (I) wherein $R^1$ is

as defined above, the starting material of Formula (I) wherein $R^1$ is hydrogen can be reacted, in an inert solvent, with 1,1'-thiocarbonyldiimidazole at room temperature or under slight heating to 50°-70° C., to obtain a reactive intermediate of the formula

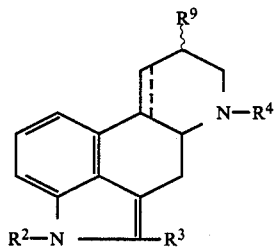

wherein
$R^2$, $R^3$, and $R^4$ are as defined above and
$R^9$ is —N=C=S or

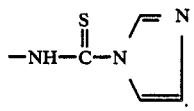

Without further isolation, this intermediate is then combined with the primary or secondary amine of the formulae $H_2NR^6$ or $HNR^5R^6$ at room temperature. The reaction mixture is heated to 50°-70° C. until the reaction is completed. The reaction is terminated after 1-3 hours, the longer reaction periods occurring when reacting with secondary amines.

Alternatively, the starting material can be combined, in an inert solvent, with an alkyl or aryl isothiocyanate of Formula (V) $R^6$—N=C=S at room temperature or under slight heating to 50°-70° C. Suitable inert solvents for conducting this process are hydrocarbons, such as hexane, toluene; halogenated hydrocarbons, such as methylene chloride; ethers, such as diisopropyl ether; esters, such as ethyl acetate, etc.

The resultant compounds of Formula (I) wherein $R^1$ is

and $R^2$ is hydrogen can optionally be conventionally acylated in the 1-position (V.O. Illi, Synthesis 1979: 387). For this purpose, the compound of Formula (I) wherein $R^2$ is H and $R^1$ is

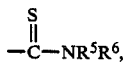

can be dissolved, for example, in methylene chloride and this solution combined with potassium hydroxide and tetrabutylammonium hydrogen sulfate, and with a reactive acid derivative, such as, for example, the acetic acid chloride, propionic acid chloride, etc.

The following compounds wherein $R^1$ is H can likewise be conventionally acylated, e.g., by first conventionally blocking the 8-position amino group and then carrying out an acylation as described above.

The thus-obtained compounds can be purified by recrystallization and/or chromatography in the form of the free bases or their acid addition salts obtained, if desired, by conventional reaction with a physiologically compatible acid, such as, for example, tartaric acid, maleic acid, benzoic acid, or any of the many others well known to those skilled in the art.

In order to form salts, for example, the resultant compounds of Formula (I) can be dissolved in a small amount of methanol or methylene chloride and combined with a concentrated solution of the desired organic acid in methanol at room temperature.

All of the starting compounds required to conduct the processes of this invention are either known or can be prepared according to methods well known to those skilled in the art. The preparation of the 8α-amines is described, e.g., by A. Hofmann, Helv. Chim. Acta 30 (1947) pp 44.

For example, compounds are suitably employed as the starting materials which are derived from naturally occurring lysergic acid derivatives.

For example, 9,10-didehydroergoline-8α-acetamide can be prepared according to the following process:

(A) 2.0 g of 9,10-didehydro-6-methylergoline-8α-amine (8.5 mmol) is dissolved in 40 ml of pyridine; under ice cooling, 3.5 ml of trichloroacetyl chloride is added thereto and thereafter the mixture is stirred at room temperature for 30 minutes. After the addition of ice, the mixture is stirred into saturated bicarbonate solution and extracted with methylene chloride. After evaporation of the solvent, 9,10-didehydro-6-methylergoline-8α-trichloroacetamide is isolated in quantitative yield.

The thus-obtained crude product is dissolved in 150 ml of anhydrous dioxane and stirred at room temperature for 2 hours with 2.4 g of anhydrous potassium carbonate and 9 g of cyanogen bromide. After distillation of the excess cyanogen bromide and part of the solvent, the mixture is taken up in methylene chloride and, after removing the potassium carbonate by filtration, extracted with water. The organic phase is dried and evaporated. The residue is chromatographed with methylene chloride and methanol. The yield is practically quantitative; the compound is oily and not quite pure.

6-Cyano-9,10-didehydroergoline-8α-trichloroacetamide is dissolved in 500 ml of glacial acetic acid and 17 ml of water and heated with 2 g of zinc acetate for 3 hours to 100° C. After adding 10 g of zinc dust, another 7 g of zinc dust is added after 3 hours, and the mixture is stirred a total of 7 hours at 100° C. After filtration over "Celite", the acetic acid is distilled off; the mixture is taken up in methylene chloride and ice and made alkaline with dilute ammonia solution. The methylene chloride phase is separated, dried, and evaporated; the aqueous phase is once more extracted with ethyl acetate, and all extracts are combined. Chromatography on silica gel with methylene chloride and methanol yields 0.87 g of 9,10-didehydroergolinyl-8α-acetamide, which is isolated.

$[\alpha]_D = \pm 0°$ (0.5% in 1N acetic acid).

(B) 950 mg of 6-cyano-9,10-didehydroergolinecarboxylic acid methyl ester (3.2 mmol) is dissolved in 100 ml of chloroform and 18 ml of anhydrous hydrazine and stirred for one hour in an ice bath and for 3 hours at room temperature. The mixture is distributed between saturated sodium chloride solution and methylene chloride; the organic phase is washed with water, dried with magnesium sulfate, and evaporated (crude product 739 mg). The product is chromatographed on silica gel with methylene chloride, ethyl acetate, and methanol, yielding the pure 6-cyano-9,10-didehydroergolinecarboxylic acid hydrazide. A solution of 950 mg (3.2 mmol) of this hydrazide in 100 ml of tetrahydrofuran is cooled in an ice bath and combined in succession with 11 ml of a saturated solution of hydrogen chloride in toluene (about 0.7N), 3.5 ml of a 1N lithium nitrite solution in tetrahydrofuran, and 22 ml of the above hydrogen chloride solution. Under ice cooling, the mixture is agitated for 20 minutes, then diluted with 140 ml of dioxane, and heated for 30 minutes in an oil bath preheated to 80° C. After cooling in an ice bath, 20 ml of 0.2N hydrochloric acid is added thereto, the mixture is allowed to stand for 20 minutes and evaporated to dryness. The residue is made into a solution with a small amount of methanol, distributed between chloroform and sodium bicarbonate, the aqueous phase is washed with chloroform, the organic phase respectively several times with water, dried with magnesium sulfate, and evaporated. 1.0 g of the crude 8-amino-6-cyano-9,10-didehydroergoline is dissolved in 15 ml of pyridine, combined with 0.6 ml of acetyl chloride, and ice is added after one hour; the mixture is distributed between saturated bicarbonate solution and methylene chloride; the organic phase is dried and evaporated.

The crude 6-cyano-9,10-didehydroergolinyl-8-acetamide is dissolved in 100 ml of glacial acetic acid, heated with 1.5 ml of water and 0.5 g of zinc acetate for 5 hours to 100° C., then 3 g of zinc dust is added and the mixture agitated for another 3 hours at 100° C. After filtration over "Celite", the mixture is washed with water and the filtrate exhaustively evaporated under vacuum. The residue is combined with methylene chloride and ice and rendered alkaline with dilute ammonia solution. After extraction, the crude product is chromatographed on a low-pressure column with methylene chloride and methanol, thus obtaining 520 mg of 9.10-didehydroergolinyl-8-acetamide.

(C) 30 g of pulverized potassium hydroxide is added to a solution of 7.65 g of 9,10-didehydroergoline-8-carboxylic acid methyl ester (28.5 mmol) and 1.22 g of tetrabutylammonium hydrogen sulfate in 900 ml of methylene chloride, and then 125 ml of trichloroethyl chloroformate is added dropwise thereto. After 15 minutes, the mixture is cooled in an ice bath, gently combined with about 300 ml of saturated sodium bicarbonate solution, and stirred for one hour. After extraction with chloroform, this phase is washed with water, dried over magnesium sulfate, and evaporated. The crude product is chromatographed on silica gel with chloroform and methanol, yielding 13.85 g (79% of theory) of 9,10-didehydro-1,6-bis(2,2,2-trichloroethoxycarbonyl)-8-ergolinecarboxylic acid methyl ester as an oily mixture of isomers.

490 mg of the ester (0.8 mmol) in 35 ml of chloroform is stirred together with 12 ml of hydrazine for 25 hours at room temperature. The mixture is then distributed between chloroform and saturated sodium chloride solution, the organic phase is dried with magnesium sulfate and evaporated. The crude product, amounting to 287 mg, is chromatographed on silica gel, thus isolating 193 mg of 9,10-didehydro-6-(2,2,2-trichloroethoxycarbonyl)-8-ergolinecarboxylic acid hydrazide as an oily mixture of isomers (55% of theory).

A solution of 3.2 mmol of the previously prepared hydrazide in 100 ml of tetrahydrofuran is cooled in an ice bath and combined in succession with 11 ml of a saturated solution of hydrogen chloride in toluene (about 0.7N), 3.5 ml of a 1N lithium nitrite solution in tetrahydrofuran, and 22 ml of the above hydrogen chloride solution. The mixture is further stirred under ice cooling for 20 minutes, then diluted with 140 ml of dioxane, and heated for 30 minutes in an oil bath preheated to 80° C. After cooling in an ice bath, 20 ml of 0.2N hydrochloric acid is added, the mixture is allowed to stand for 20 minutes and evaporated to dryness. The residue is dissolved with a small amount of methanol, distributed between chloroform and sodium bicarbonate, the aqueous phase is washed with chloroform, the organic phase respectively several times with water, dried with magnesium sulfate, and evaporated. The crude product is chromatographed on silica gel. The resultant 8-amino-9,10-didehydro-6-(2,2,2-trichloroethoxycarbonyl)ergoline is acetylated as described in method (A) with acetyl chloride in pyridine. A solution is prepared from 1.1 g of this 9,10-didehydro-6-(2,2,2-trichloroethoxycarbonyl)ergoline acetamide in 130 ml of glacial acetic acid. Under heating to 70° C., a total of 8.5 g of zinc powder is added thereto in incremental portions.

After 2 hours, the mixture is filtered off from excess zinc, washed with chloroform, and evaporated to dryness. Chromatography yields 518 mg of 9,10-didehydroergoline-8-acetamide.

For conversion of the 9,10-didehydroergoline compounds into the corresponding 9,10-saturated compounds, the alkali metal reduction is preferably utilized, as will be demonstrated using an example the preparation of 6-methylergoline-8α-amine from the 9,10-didehydro compound:

25 ml of anhydrous ammonia (distilled over sodium) is cooled to −70° C. and then used for the reaction. After adding 598 mg of 9,10-didehydro-6-methylergoline-8α-amine (2.5 mmol) and 0.35 ml of aniline, lithium is introduced in incremental portions into the resultant suspension within 45 minutes. The blue coloration becomes permanent toward the end of the reaction (lithium consumed: 86.5 mg). After further agitation for 10 minutes, the blue coloring is destroyed with ammonium chloride, the ammonia is evaporated, the residue is taken up in 50 ml of ethyl acetate and washed once with 50 ml and once with 20 ml of 16% strength aqueous ammonia solution. The washing liquid is utilized for rinsing the reaction flask. Subsequently the mixture is extracted with 25 ml of ethyl acetate. The combined ethyl acetate phases are dried and evaporated to dryness under vacuum at 30° C.

Yield: 506.8 mg of 6-methylergoline-8α-amine (84% of theory), mp >265° C. (methanol/methylene chloride).

$[\alpha]_D = -59.4°$ (c=0.5, methanol/methylene chloride 1:1).

The aforedescribed alkali metal reduction can also be conducted after previous acetylation of the 8-amino group, as will be demonstrated by the following example wherein 8-acetamidoergoline is prepared, subsequently to the reduction, from 6-methyl-8-acetamidoergoline:

Under ice cooling, 5.98 g of 9,10-didehydro-6-methylergoline-8α-amine (25 mmol) in 125 ml of pyridine is combined with 2 ml of acetyl chloride. After stirring for 2 hours at room temperature, ice is added and the mixture extracted with methylene chloride. The organic phase is dried and evaporated to dryness under vacuum. The yield is almost quantitative.

$[α]_D = +381°$ (0.5% in pyridine).

The crude 9,10-didehydro-6-methylergoline-8α-acetamide is dissolved in 130 ml of freshly distilled, anhydrous tetrahydrofuran. This solution is added dropwise to a solution of 3.6 ml of distilled aniline in 250 ml of distilled, anhydrous ammonia to such an extent that the addition of small pieces of lithium evokes a weak blue coloring in all cases. Within about one hour, 580 mg of lithium is used up; the mixture is then stirred for 5 minutes and decolorized with ammonium chloride. After the ammonia has been removed by evaporation, the residue is distributed between methylene chloride and saturated bicarbonate solution, the organic phase is dried and evaporated. Recrystallization from methanol yields 6.69 g of 6-methylergoline-8α-acetamide (94% of theory).

$[α]_D = +14°$ (0.5% in pyridine).

A solution is prepared from 350 ml of anhydrous dioxane and 6.0 g of the previously prepared compound (21 mmol); 5.6 g of anhydrous potassium carbonate and 22 g of cyanogen bromide are added, and the mixture is stirred for 5 hours at room temperature. The excess cyanogen bromide is distilled off under vacuum together with part of the solvent. The potassium carbonate is filtered off, and the solution is then evaporated to dryness. The residue is dissolved in methylene chloride and ethyl acetate; this solution is extracted with water, dried, and evaporated. The resultant 6-cyanoergoline-8α-acetamide is obtained in quantitative yield and of sufficient purity for further processing.

$[α]_D = +100°$ (0.5% in chloroform).

A solution of 6-cyanoergoline-8α-acetamide in 150 ml of anhydrous tetrahydrofuran is introduced dropwise into 200 ml of freshly distilled, anhydrous ammonia. Then 3.9 g of potassium is added in small pieces until the blue color is permanent. After 2 minutes of agitation, 30 ml of methanol is added dropwise, the ammonia is removed by evaporation, and the residue is taken up in ethyl acetate. The solution is extracted with saturated sodium chloride solution, the organic phase is dried and evaporated, thus obtaining ergoline-8α-acetamide in a yield of 89% of theory.

$[α]_D = +56°$ (0.5% in pyridine).

The reactions described in the above exemplary preparation directions permit, when appropriately combined, the production of all of the starting compounds required for the process of this invention. Depending upon the desired substituents and routinely selected reaction conditions, the compounds of Formula (I) isomeric in the 8-position can occurr in mixtures or as impurity amounts; in all cases they can be conventionally separated by means of physicochemical purification procedures.

Without further elaboration, it is believed that one skilled in the art can, using the proceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celcius; unless otherwise indicated, all parts and percentages are by weight.

EXAMPLE 1

At room temperature, 750 mg of pulverized potassium hydroxide, 60 mg of tetrabutylammonium hydrogen sulfate, and 1.5 ml of methyl iodide are added to a solution of 421 mg of 9,10-didehydro-6-methylergoline-8α-acetamide (1.5 mmol) in 30 ml of anhydrous tetrahydrofuran; the mixture is stirred for 2 hours. Then the mixture is filtered off from the precipitate, washed with methylene chloride, and evaporated to dryness. The residue is distributed between methylene chloride and saturated bicarbonate solution; the organic phase is separated, dried, and concentrated. The residue is chromatographed on silica gel with methylene chloride and methanol, thus isolating 9,10-didehydro-1,6-dimethylergoline-8α-acetamide in a 73% yield. This product is dissolved in 8 ml of anhydrous hydrazine and heated together with 250 mg of hydrazine dihydrochloride for 24 hours under a protective gas to 80° C. The mixture is taken up in methylene chloride and water, the organic phase is dried and evaporated, thus obtaining crude 9,10-didehydro-1,6-dimethylergoline-8α-amine which is purified by gradient chromatography.

Yield: 260 mg (65% of theory).

$[α]_D = +225°$ (c=0.5% in pyridine).

Analogously, 6-methylergoline-8α-acetamide yields 1,6-dimethylergoline-8α-amine in an 83% yield.

$[α]_D = -44°$ (c=0.5% in pyridine).

EXAMPLE 2

718 mg of 9,10-didehydro-6-methylergoline-8α-amine (3 mmol) is dissolved in 75 ml of dioxane freshly distilled over lithium aluminum hydride. Then 1,955 mg of pyrrolidone hydroperbromide (6 mmol) is introduced in incremental portions within 5 minutes into the reaction mixture at room temperature under agitation and exclusion of moisture while passing nitrogen through the mixture. After 30 minutes, 10 ml of acetone is added; after another 10 minutes, 25 ml of 32% aqueous ammonia solution is introduced. With the addition of sodium chloride, ethyl acetate is used to extract the reaction mixture. The organic phase, dried over magnesium sulfate, is evaporated under vacuum, the evaporation residue is chromatographed over silica gel by the gradient method with methanol/water 98:2 against methanol/aqueous 32% ammonia solution 98:2. Besides unreacted starting material, 787 mg of 2-bromo-9,10-didehydro-6-methylergoline-8α-amine is obtained (60% of theory).

$[α]_D = +175°$ (c=0.5% in pyridine).

Analogously, 483 mg of 6-methylergoline-8α-amine yields 506 mg of 2-bromo-6-methylergoline-8α-amine (79% of theory), mp >275° C. (decomposition).

$[α]_D = -80.8°$ (c=0.5% in methanol).

EXAMPLE 3

369 mg of 9,10-didehydroergolinyl-8α-acetamide (1.4 mmol) in 30 ml of nitromethane is combined with 600 mg of anhydrous potassium carbonate, 110 mg of tetrabutylammonium hydrogen sulfate, and 1 ml of propyl iodide, and the mixture is stirred for 30 hours at room temperature. The solvent is exhaustively removed by distillation, the residue is distributed between methylene chloride and water, and the organic phase is separated. The latter is dried, evaporated, and the 9,10-didehydro-6-n-propylergolinyl-8α-acetamide is dissolved in 8 ml of anhydrous hydrazine and heated to 80° C. together with 250 mg of hydrazine dihydrochloride for 24 hours under an inert gas. The mixture is taken up in methylene chloride and water, the organic phase is dried and evaporated, thus producing 9,10-didehydro-6-n-propylergoline-8α-amine.

Yield: 250 mg (67% of theory).
$[\alpha]_D = +127°$ (c=0.5% in pyridine).

Analogously, the following compounds are produced:

9,10-Didehydro-6-ethylergoline-8α-amine (by alkylation with ethyl iodide).
Yield: 66% of theory.
$[\alpha]_D = +136°$ (c=0.5% in methanol).

6-Cyclopropylmethyl-9,10-didehydroergoline-8α-amine (by alkylation with cyclopropylmethyl iodide).
Yield: 80% of theory.
$[\alpha]_D = 121°$ (c=0.5% in methanol).

According to the same method, ergoline-8α-acetamide is used and alkylated with ethyl iodide, n-propyl iodide, alkyl bromide, or cyclopropylmethyl iodide, thus obtaining, in each case after purification by chromatography:

6-Ethylergoline-8a-amine;
yield: 86% of theory,
$[\alpha]_D = -59°$ (c=0.5% in methanol).
6-n-Propylergoline-8α-amine;
yield: 74% of theory,
$[\alpha]_D = -41°$ (c=0.5% in pyridine).
6-Allylergoline-8α-amine;
yield: 74% of theory,
$[\alpha]_D = -74.5°$ (c=0.5% in methanol).
6-Cyclopropylmethylergoline-8α-amine;
yield: 85% of theory,
$[\alpha]_D = 49°$ (c=0.5% in methanol).

EXAMPLE 4

10 Millimoles of 6-ethyl-lysergic acid (isolysergic acid) hydrazide as an isomeric mixture in the 8-position is dissolved in 50 ml of 0.2N hydrochloric acid; 10 ml of 1N sodium nitrite solution and another 60 ml of 0.2N hydrochloric acid are added to the reaction mixture. These operations are conducted under ice cooling, the solutions having been cooled previously. The mixture is stirred for 2 minutes, combined with 250 ml of cold toluene and 80 ml of 1N ammonia solution, and thoroughly extracted. The phases are separated, shaken three times with 250 ml of toluene for extraction purposes, and the combined organic phases are dried with sodium sulfate. This solution is heated under agitation for 15 minutes in an oil bath preheated to 100° C., then cooled, and combined with 200 ml of 0.2N hydrochloric acid. The mixture is stirred for one hour at room temperature, the phases are separated, and the aqueous phase is heated for 20 minutes in an oil bath preheated to 100° C. The cooled solution is made alkaline with soda solution and extracted with methylene chloride. This phase is dried with sodium sulfate, evaporated, leaving as the residue the 6-ethylergoline-8-amine as a mixture of isomers, which can be separated by chromatography into 8α- and 8β-amine. The yield is 21% of theory.

EXAMPLE 5

239.3 mg of 9,10-didehydro-6-methylergoline-8α-amine (1 mmol) is dissolved in 5 ml of anhydrous methylene chloride. Under a nitrogen atmosphere, 150 mg of methyl isothiocyanate (2.05 mmol), dissolved in 5 ml of anhydrous methylene chloride, is added dropwise to the reaction mixture, and the latter is allowed to react under reflux conditions for one hour. Subsequently the cooled reaction solution, which has been diluted with 50 ml of methylene chloride, is washed twice with respectively 10 ml of 16% aqueous ammonia solution, then washed with 25 ml of saturated aqueous sodium chloride solution, and dried over magnesium sulfate. The residue, remaining after evaporation of the methylene chloride phase (272 mg), consisting of 3-(9,10-didehydro-6-methyl-8α-ergolinyl)-1-methylthiourea, is taken up in 10 ml of ethanol, a solution of 110 mg of maleic acid (1.1 molar equivalents) dissolved in 5 ml of ethanol is added thereto, the mixture is evaporated to two-thirds its volume, and allowed to crystallize in a refrigerator, thus isolating 286 mg of 3-(9,10-didehydro-6-methyl-8α-ergolinyl)-1-methylthiourea hydrogen maleate, mp 193° C. (decomposition).
$[\alpha]_D = +351.8°$ (c=0.5% in pyridine).

EXAMPLE 6

Analogously to Example 5, 359 mg of 9,10-didehydro-6-methylergoline-8β-amine (1.5 mmol) yields 417 mg of 3-(9,10-didehydro-6-methyl-8β-ergolinyl)-1-methylthiourea, mp 221° C. (decomposition).
$[\alpha]_D = +120.6°$ (c=0.5% in pyridine).

After reaction with maleic acid, the compound is isolated as the hydrogen maleate in an 88% yield, mp 190° C. (decomposition).
$[\alpha]_D = +91.8°$ (c=0.5% in pyridine).

EXAMPLE 7

As described in Example 5, reaction of 359 mg of 9,10-didehydro-6-methylergoline-8α-amine (1.5 mmol) with 174 mg of ethyl isothiocyanate (2 mmol) yields 504.5 mg of 3-(9,10-didehydro-6-methyl-8α-ergolinyl)-1-ethylthiourea hydrogen maleate, mp 195° C. (decomposition).
$[\alpha]_D = +328.6°$ (c=0.5% in pyridine).

EXAMPLE 8

As indicated in Example 7, 9,10-didehydro-6-methylergoline-8β-amine is used to isolate 3-(9,10-didehydro-6-methyl-8β-ergolinyl)-1-ethylthiourea in a yield of 78% of theory (based on amine employed), mp 214° C. (decomposition).
$[\alpha]_D = +110.4°$ (c=0.5% in pyridine).

Reaction with maleic acid produces the hydrogen maleate in a 69% yield, mp 193° C. (decomposition).
$[\alpha]_D = +76.2°$ (c=0.5% in pyridine).

EXAMPLE 9

359 mg of 9,10-didehydro-6-methylergoline-8α-amine (1.5 mmol) is suspended in 7.5 ml of anhydrous methylene chloride while passing nitrogen through the mixture. At room temperature, 294 mg of 1,1'-thiocarbonyldiimidazole (1.65 mmol), dissolved in 7.5 ml of anhydrous methylene chloride, is added dropwise within 3 minutes. After one hour of agitation, the mixture is heated to 50° C. and dimethylamine is introduced for one hour. The cooled reaction solution is then vigorously stirred with 10 ml of distilled water, the aqueous phase is separated and extracted twice with respectively 25 ml of methylene chloride.

The combined organic phases are washed once with 20 ml of saturated sodium chloride solution, dried over sodium sulfate, and evaporated to dryness under vacuum at 30° C., thus obtaining 495 mg of 3-(9,10-didehydro-6-methyl-8α-ergolinyl)-1,1-dimethylthiourea as an oil and therefrom, respectively, 491 mg of the compound as the hydrogen maleate, mp 186° C. (decomposition).

$[\alpha]_D = +271.2°$ (c=0.5% in pyridine).

EXAMPLE 10

Under the reaction conditions set forth in Example 9, 1.5 mmol of 9,10-didehydro-6-methylergoline-8β-amine yields 3-(9,10-didehydro-6-methyl-8β-ergolinyl)-1,1-dimethylthiourea, mp 195° C. (decomposition), with a yield of 91% of theory, and from this, in a 73% yield (based on 8β-amine utilized), the hydrogen maleate, mp 166° C. (decomposition).

$[\alpha]_D = +125.2°$ (c=0.5% in pyridine).

EXAMPLE 11

As indicated in Example 9, 359 mg of 9,10-didehydro-6-methylergoline-8α-amine (1.5 mmol) is converted into the corresponding 8α-isothiocyanate with 1,1'-thiocarbonyldiimidazole. At room temperature, 0.5 ml of freshly distilled diethylamine is added dropwise thereto; the mixture is allowed to react for 2 hours at room temperature under an inert gas atmosphere, and worked up as disclosed in Example 9. The evaporation residue is filtered with methylene chloride/water 99:1 over silica gel. Yield: 414.8 mg of 3-(9,10-didehydro-6-methyl-8α-ergolinyl)-1,1-diethylthiourea, mp 157°–158° C. (decomposition).

$[\alpha]_D = +377.0°$ (c=0.5% in pyridine).

By forming the salt of diethylthiourea with maleic acid, 468 mg of hydrogen maleate is obtained, mp 183° C. (decomposition).

$[\alpha]_D = +283.8°$ (c=0.5% in pyridine).

EXAMPLE 12

By reaction of 9,10-didehydro-6-methylergoline-8β-amine with 1,1'-thiocarbonyldiimidazole and diethylamine analogously to Example 11, 3-(9,10-didehydro-6-methyl-8β-ergolinyl)-1,1-diethylthiourea is obtained, mp 207° C. (decomposition) and, respectively, therefrom the hydrogen maleate in a 74.7% yield (based on the 8β-amine), mp 180° C. (decomposition).

$[\alpha]_D = +140.9°$ (c=0.5% in pyridine).

EXAMPLE 13

By reaction of 656 mg of 2-bromo-9,10-didehydro-6-methylergoline-8α-amine (1.5 mmol) with 1,1'-thiocarbonyldiimidazole and diethylamine, as described in Example 11, 535 mg of 3-(2-bromo-9,10-didehydro-6-methyl-8α-ergolinyl)-1,1-diethylthiourea is obtained.

$[\alpha]_D = +46°$ (c=0.5% in methanol).

This compound is converted, by salt formation with L(+)-tartaric acid, into 3-(2-bromo-9,10-didehydro-6-methyl-8α-ergolinyl)-1,1-diethylthiourea L-hydrogen tartrate, yield: 417 mg (71% of theory), mp 205° C. (decomposition).

$[\alpha]_D = +340.8°$ (c=0.5% in pyridine).

EXAMPLE 14

One millimole (241 mg) of 6-methylergoline-8α-amine is reacted analogously to Example 11 to 3-(6-methyl-8α-ergolinyl)-1,1-diethylthiourea, yield: 244 mg (68.4% of theory), mp 217° C. (decomposition; ethyl acetate/ether).

$[\alpha]_D = +35.0°$ (c=0.5% in pyridine).

By adding piperidine, N-methylpiperazine and 4-fluoroaniline, respectively, in place of diethylamine, the following thioureas are analogously obtained as the free bases and/or by dissolution with the equivalent amount of maleic acid or L-tartaric acid and methylene chloride and/or methonol, the corresponding hydrogen maleates or L-hydrogen tartrates are produced.

Piperidine-1-thiocarboxylic acid (6-methyl-8α-ergolinyl)amide; 68% of theory; mp 210° C. (decomposition).

$[\alpha]_D = +4.8°$ (c=0.5% in methanol).

1-(4-Fluorophenyl)-3-(6-methyl-8α-ergolinyl)thiourea, L-tartrate; 81% of theory; mp 260° C. (decomposition).

$[\alpha]_D = +17.6°$ (c=0.5% in pyridine).

4-Methylpiperazine-1-thiocarboxylic acid (6-methyl-8α-ergolinyl)amide; 74% of theory; mp 220° C. (decomposition).

$[\alpha]_D = +1.8°$ (c=0.5% in pyridine).

EXAMPLE 15

Analogously to Example 11, 1 mmol of 2-bromo-6-methylergoline-8α-amine yields 3-(2-bromo-6-methyl-8α-ergolinyl)-1,1-diethylthiourea.

Yield: 352.5 mg (81% of theory).

$[\alpha]_D = +46.2°$ (c=0.5% in methanol).

The L-hydrogen tartrate of the base melts at 180°–182° C. (decomposition).

EXAMPLE 16

9,10-Didehydro-6-methylergoline-8α-amine (1 mmol) is reacted analogously to Example 11 with 1,1'-thiocarbonyldiimidazole and the corresponding amine.

(a) With diallyl amine, 3-(9,10-didehydro-6-methyl-8α-ergolinyl)-1,1-bis(2-propen-1-yl)thiourea is obtained.

Yield: 72% of theory.

L-Hydrogen tartrate, 93% of theory, mp 154° C. (decomposition).

$[\alpha]_D = +228.2°$ (c=0.5% in methanol).

(b) With pyrrolidine, pyrrolidine-1-thiocarboxylic acid (9,10-didehydro-6-methyl-8α-ergolinyl)amide is obtained.

Yield: 78% of theory, mp 138° C. (decomposition).

$[\alpha]_D = +248.8°$ (c=0.5% in methanol).

(c) With morpholine, morpholine-4-thiocarboxylic acid (9,10-didehydro-6-methyl-8α-ergolinyl)amide is obtained.

Yield: 85% of theory, mp 120° C. (decomposition).

$[\alpha]_D = +235°$ (c=0.5% in pyridine).

L-Hydrogen tartrate, 89% of theory, mp 167° C. (decomposition).

$[\alpha]_D = +235°$ (c=0.5% in pyridine).

(d) With (2S)-2-hydroxymethylpyrrolidine, (2S)-2-hydroxymethylpyrrolidine-1-thiocarboxylic acid (9,10-didehydro-6-methyl-8α-ergolinyl)amide is produced.

Yield: 83% of theory, mp 130° C. (decomposition).

$[\alpha]_D = +203.6°$ (c=0.5% in pyridine).

Hydrogen maleate, 65% of theory, mp 196° C. (decomposition).

$[\alpha]_D = +175.8°$ (c=0.5% in pyridine).

(e) With thiomorpholine, 3,4,5,6-tetrahydro-2H-1,4-thiazine-4-thiocarboxylic acid (9,10-didehydro-6-methyl-8α-ergolinyl)amide is obtained.

Yield: 83% of theory, mp 97°–108° C. (decomposition).

$[\alpha]_D = +320.4°$ (c=0.5% in pyridine).

Hydrogen maleate, 69% of theory, mp 148° C. (decomposition).

$[\alpha]_D = +236.4°$ (c=0.5% in pyridine).

EXAMPLE 17

A solution is prepared from 354 mg of 3-(9,10-didehydro-6-methyl-8α-ergolinyl)-1,1-diethylthiourea in 20 ml of methylene chloride. This solution is added to 0.5 g of pulverized potassium hydroxide and 40 ml of tetrabutylammonium hydrogen sulfate; 0.2 ml of acetyl chloride is added to this mixture. After one hour of agitation at room temperature, saturated bicarbonate solution and more methylene chloride are added, the organic phase is separated, dried, and evaporated. The residue is separated by chromatography, thus obtaining 3-(1-acetyl-9,10-didehydro-6-methyl-8α-ergolinyl)-1,1-diethylthiourea.

Yield: 123 mg (31% of theory).
$[\alpha]_D = +342°$ (c=0.5% in pyridine).

EXAMPLE 18

One millimole of 9,10-didehydro-1,6-dimethylergoline-8α-amine is reacted with 1,1'-thiocarbonyldiimidazole and diethylamine, as described in Example 11, to 3-(9,10-didehydro-1,6-dimethyl-8α-ergolinyl)-1,1-diethylthioruea. After chromatography, 3-(9,10-didehydro-1,6-dimethyl-8α-ergolinyl)-1,1-diethylthiourea is obtained in a 67% yield. By dissolution with the equivalent quantity of L-tartaric acid in methylene chloride and methanol, 3-(9,10-didehydro-1,6-dimethyl-8α-ergolinyl)-1,1-diethylthiourea tartrate is obtained.

Yield: 226 mg (51% of theory).
$[\alpha]_D = +296°$ (c=0.5% in pyridine).

EXAMPLE 19

By reaction of the saturated or unsaturated amino compounds with 1,1'-thiocarbonyldiimidazole and subsequent addition of a primary or secondary amine, such as diethylamine, the corresponding thioureas are produced as described in Example 11.

(a) 3-(9,10-Didehydro-6-ethyl-8α-ergolinyl)-1,1-diethylthiourea as the L-hydrogen tartrate,
yield: 45% of theory.
$[\alpha]_D = +209°$ (c=0.5% in pyridine).

(b) 3-(9,10-Didehydro-6-n-propyl-8α-ergolinyl)-1,1-diethylthiourea,
yield: 73% of theory.
L-Tartrate; yield: 80% of theory.
$[\alpha]_D = +231°$ (c=0.5% in pyridine).

(c) 3-(6-Cyclopropylmethyl-9,10-didehydro-8α-ergolinyl)-1,1-diethylthiourea,
yield: 38% of theory.
L-Tartrate; yield: 65% of theory.
$[\alpha]_D = +266°$ (c=0.5% in pyridine).

(d) 1,1-Diethyl-3-(6-ethyl-8α-ergolinyl)thiourea,
yield: 57% of theory.
$[\alpha]_D = +40°$ (c=0.5% in chloroform).

(e) 3-(6-n-Propyl-8α-ergolinyl)-1,1-diethylthiourea,
yield: 74% of theory.
$[\alpha]_D = +42°$ (c=0.5% in chloroform).

(f) 3-(6-Allyl-8α-ergolinyl)-1,1-diethylthiourea,
yield: 98% of theory.
L-Tartrate; yield: 70% of theory.
$[\alpha]_D = +38°$ (c=0.5% in pyridine).

(g) 3-(6-Cyclopropylmethyl-8α-ergolinyl)-1,1-diethylthiourea,
yield: 68% of theory.
L-Tartrate; yield: 88% of theory.
$[\alpha]_D = +42°$ (c=0.5% in pyridine).

The free bases can be converted into the tartrates by dissolving with the equivalent amount of L-tartaric acid in methylene chloride and methanol.

EXAMPLE 20

Analogously to Example 11, 300 mg of 1,6-dimethylergoline-8α-amine yields, with 1,1'-thiocarbonyldiimidazole and diethylamine, 274 mg of 1,1-diethyl-3-(1,6-dimethyl-8α-ergolinyl)thiourea.

Yield: 63% of theory.
$[\alpha]_D = +38°$ (c=0.5% in chloroform).

The preceeding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An ergolinyl compound, which is nitrogen-substituted in the 8-position, of the formula

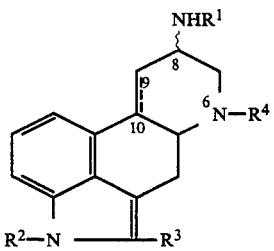

or a physiologically compatible salt thereof, wherein
$R^1$ is

and the 8-substituent is in the α- or β-position,

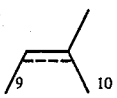

is a single or double bond, $R^2$ is hydrogen, $C_{1-4}$-alkyl or a $C_{1-7}$-acyl group derived from a $C_{1-7}$-hydrocarbon carboxylic or sulfonic acid;

$R^3$ is hydrogen, chlorine or bromine; and $R^4$ is $C_{1-6}$-alkyl, $C_{3-6}$-cycloalkyl-$C_{1-3}$-alkyl, $C_{3-6}$-alkenyl, or $C_{2-6}$-alkynyl;

$R^5$ is hydrogen, $C_{1-10}$-alkyl, $C_{3-10}$-alkenyl, or $C_{3-10}$-alkynyl, $R^6$ is $C_{1-10}$-alkyl, $C_{3-10}$-alkenyl, $C_{3-10}$-alkynyl, $C_{6-10}$-aryl or $C_{6-10}$-aryl substituted by $C_{1-4}$-alkyl, $C_{1-4}$-alkoxy, F, Cl or Br, or $R^5$ and $R^6$ together with the connecting N-atom form a 5- to 10-membered aliphatic, saturated cyclic ring whose remaining members are C-atoms, or form such a ring wherein a —CH$_2$-ring member is replaced by O, N or S.

2. A compound of claim 1 wherein $R^4$ is $C_{1-3}$-alkyl or $C_{3-6}$-cycloalkyl-$C_{1-2}$-alkyl.

3. A compound of claim 1 wherein
$R^4$ is $CH_3$, n-propyl or

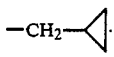

4. A compound of claim 1 wherein $R^2$ is H, $R^3$ is H or halo and $R^5$ and $R^6$ are H, $CH_3$ or $C_2H_5$.

5. A compound of claim 3 wherein $R^2$ is H, $R^3$ is H or halo and $R^5$ and $R^6$ are H, $CH_3$ or $C_2H_5$.

6. A compound of claim 1 wherein

is a double bond.

7. A compound of claim 1 wherein $R^1$ is $CSNR^5R^6$ wherein $R^5/R^6$ are $H/CH_3$, $H/C_2H_5$, $CH_3/CH_3$ or $C_2H_5/C_2H_5$.

8. A compound of claim 1 wherein $R^1$ is $CSN(C_2H_5)_2$.

9. 3-(9,10-didehydro-6-methyl-8α-ergolinyl)-1-methylthiourea, a compound of claim 1.

10. 3-(9,10-didehydro-6-methyl-8α-ergolinyl)-1-ethylthiourea, a compound of claim 1.

11. 3-(9,10-didehydro-6-methyl-8α-ergolinyl)-1,1-dimethylthiourea, a compound of claim 1.

12. 3-(9,10-didehydro-6-methyl-8α-ergolinyl)-1,1-diethylthiourea, a compound of claim 1.

13. 3-(2-bromo-9,10-didehydro-6-methyl-8α-ergolinyl)-1,1-diethylthiourea, a compound of claim 1.

14. 3-(6-methyl-8α-ergolinyl)-1,1-diethylthiourea, a compound of claim 1.

15. 3-(2-bromo-6-methyl-8α-ergolinyl)-1,1-diethylthiourea, a compound of claim 1.

16. 3,4,5,6-tetrahydro-2H-1,4-thiazine-4-thiocarboxylic acid (9,10-didehydro-6-methyl-8αergolinyl)-amide, a compound of claim 1.

17. 3-(9,10-didehydro-6-n-propyl-8α-ergolinyl)-1,1-diethylthiourea, a compound of claim 1.

18. 3-(6-cyclopropylmethyl-9,10-didehydro-8α-ergolinyl)-1,1-diethylthiourea, a compound of claim 1.

19. 3-(6-n-propyl-8α-ergolinyl)-1,1-diethylthiourea, a compound of claim 1.

20. 3-(6-cyclopropylmethyl-8α-ergolinyl)-1,1-diethylthiourea, a compound of claim 1.

21. A compound of claim 1 wherein:
$R^1$ is $-CSNR^5R^6$.

22. A compound of claim 1 wherein $R^4$ is alkenyl or alkynyl.

23. A compound of claim 1 wherein $R^2$ is acyl.

24. A compound of claim 1 wherein

is a double bond.

25. A compound of claim 21 wherein $R^4$ is alkenyl or alkynyl.

26. A compound of claim 21 wherein $R^2$ is acyl.

27. A compound of claim 21 wherein $R^3$ is Cl or Br.

28. A compound according to claim 1, which is unsubstituted in the 1- and 2-positions or substituted in only one of the 1- or 2-positions.

29. A pharmaceutical composition comprising a dopaminergically or antidopaminergically effective amount of a compound of the formula

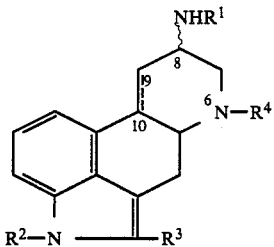

or a physiologically compatible salt thereof, wherein $R^1$ is

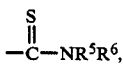

and the 8-substituent is in the α- or β-position,

is a single or double bond, $R^2$ is hydrogen, $C_{1-4}$-alkyl or a $C_{1-7}$-acyl group derived from a $C_{1-7}$-hydrocarbon carboxylic or sulfonic acid;

$R^3$ is hydrogen, chlorine or bromine; and $R^4$ is $C_{1-6}$-alkyl, $C_{3-6}$-cycloalkyl-$C_{1-3}$-alkyl, $C_{3-6}$-alkenyl, or $C_{2-6}$-alkynyl;

$R^5$ is hydrogen, $C_{1-10}$-alkyl, $C_{3-10}$-alkenyl, or $C_{3-10}$-alkynyl, $R^6$ is $C_{1-10}$-alkyl, $C_{3-10}$-alkenyl, $C_{3-10}$-alkynyl, $C_{6-10}$-aryl or $C_{6-10}$-aryl substituted by $C_{1-4}$-alkyl, $C_{1-4}$-alkoxy, F, Cl or Br, or $R^5$ and $R^6$ together with the connecting N-atoms form a 5- to 10-membered aliphatic, saturated cyclic ring whose remaining members are C-atoms, or form such a ring wherein a —$CH_2$-ring member is replaced by O, N or S, and a pharmaceutically acceptable carrier.

30. A method of treating dopamine deficiency in a patient in need of such treatment comprising administering a dopaminergically effective amount of a compound of the formula

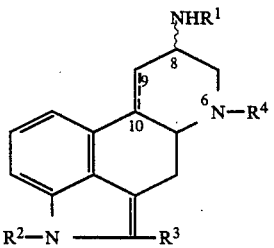

or a physiologically compatible salt thereof, wherein $R^1$ is

and the 8-substituent is in the α- or β-position,

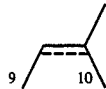

is a single or double bond, $R^2$ is hydrogen, $C_{1-4}$-alkyl or a $C_{1-7}$-acyl group derived from a $C_{1-7}$-hydrocarbon carboxylic or sulfonic acid;

$R^3$ is hydrogen, chlorine or bromine; and $R^4$ is $C_{1-6}$-alkyl, $C_{3-6}$-cycloalkyl-$C_{1-3}$-alkyl, $C_{3-6}$-alkenyl, or $C_{2-6}$-alkynyl;

$R^5$ is hydrogen, $C_{1-10}$-alkyl, $C_{3-10}$-alkenyl, or $C_{3-10}$-alkynyl, $R^6$ is $C_{1-10}$-alkyl, $C_{3-10}$-alkenyl, $C_{3-10}$-alkynyl, $C_{6-10}$-aryl or $C_{6-10}$-aryl substituted by $C_{1-4}$-alkyl, $C_{1-4}$-alkoxy, F, Cl or Br, or $R^5$ and $R^6$ together with the connecting N-atom form a 5- to 10-membered aliphatic, saturated cyclic ring whose remaining members are C-atoms, or form such a ring wherein a —$CH_2$-ring member is replaced by O, N or S.

31. A method of claim 30 wherein the patient is suffering from parkinsonism.

* * * * *

UNITED STATES PATENT AND TRADEMARK OFFICE
CERTIFICATE OF CORRECTION

PATENT NO. : 4,826,852
DATED : May 2, 1989
INVENTOR(S) : Gregor Haffer et al

It is certified that error appears in the above-identified patent and that said Letters Patent is hereby corrected as shown below:

Title Page, 6th Inventor is missing: should read "Hans-Peter Lorenz, Berlin, Fed. Rep. of Germany"

Column 19, line 41: reads "lic acid(9,10-didehydro-6-methyl-8α-ergolinyl)-amide, a"

should read -- lic acid(9,10-didehydro-6-methyl-8α-ergolinyl) amide, a --

Signed and Sealed this

Eighth Day of August, 1989

Attest:

DONALD J. QUIGG

Attesting Officer

Commissioner of Patents and Trademarks